US00PP13725P39

(12) United States Plant Patent
Watanabe et al.

(10) Patent No.: US PP13,725 P3
(45) Date of Patent: Apr. 15, 2003

(54) VERBENA PLANT NAMED 'SUNVIVABURA'

(75) Inventors: Yuki Watanabe, Kashiwa (JP); Ryuichi Tachibana, Kawasaki (JP)

(73) Assignee: Suntory Limited, Osaka (JP)

( * ) Notice: Subject to any disclaimer, the term of this patent is extended or adjusted under 35 U.S.C. 154(b) by 0 days.

(21) Appl. No.: 10/021,254

(22) Filed: Dec. 19, 2001

(65) Prior Publication Data

US 2002/0053100 P1 May 2, 2002

Related U.S. Application Data

(63) Continuation of application No. 09/375,361, filed on Aug. 17, 1999, now abandoned.

(51) Int. Cl.[7] ..... A01H 5/00
(52) U.S. Cl. ..... Plt./308
(58) Field of Search ..... Plt./308

(56) References Cited

U.S. PATENT DOCUMENTS

| | | | | |
|---|---|---|---|---|
| PP8,995 | P | 11/1994 | Tachibana et al. | Plt./308 |
| PP9,014 | P | 12/1994 | Tachibana et al. | Plt./308 |
| PP9,059 | P | 2/1995 | Tachibana et al. | Plt./308 |
| PP9,085 | P | 3/1995 | Tachibana et al. | Plt./308 |
| PP9,121 | P | 4/1995 | Tachibana et al. | Plt./308 |
| PP9,411 | P | 12/1995 | Tachibana et al. | Plt./308 |
| PP10,311 | P | 3/1998 | Tachibana | Plt./308 |
| PP10,705 | P | 11/1998 | Tachibana | Plt./308 |
| PP10,743 | P | 1/1999 | Nagase | Plt./308 |
| PP10,755 | P | 1/1999 | Nagase | Plt./308 |
| PP10,801 | P | 2/1999 | Nagase | Plt./308 |
| PP11,037 | P | 8/1999 | Yomo et al. | Plt./308 |

OTHER PUBLICATIONS

GTITM UPOVROM Citation for 'Sunvivabura' as per JP PBR 8243; Oct. 30, 1995.*

* cited by examiner

*Primary Examiner*—Kent Bell
(74) *Attorney, Agent, or Firm*—Burns, Doane, Swecker & Mathis, LLP

(57) ABSTRACT

Disclosed herein is a Verbena plant which has an erect growth habit and good plant height. The plant abundantly forms flowers in a spike with a great profusion of blooms. The blooming period is late April to November and the flowering duration is long. The whole plant remains in bloom for a considerable period of time. The flower size is large and the petal color is light purplish pink with further lightening towards the center. The plant is highly tolerant to heat and cold, and has high resistance to pests and diseases, particularly powdery mildew, and a high resistance to rain.

2 Drawing Sheets

This is a continuation of application No. 09/375,361, filed on Aug. 17, 1999 abn.

BOTANICAL/COMMERCIAL CLASSIFICATION

*Verbena hybrida*×*peruviana*/Verbana Plant

VARIETAL DENOMINATION cv. 'Sunvivabura'

BACKGROUND OF THE VARIETY

Verbena is a very popular plant and is used for flower bedding and potting in the summer season. There are only a few varieties of Verbena plants which have abundant branching, many flowers in a spike, a long flowering duration and which have a high resistance to rain, heat, cold, and disease. Accordingly, this invention was aimed at obtaining a new variety having an erect growth habit, strong branching, many flowers in a spike, large diameter flowers, a high tolerance to heat and cold, and resistances to diseases and pests, and also having petals that are light purplish pink.

The new variety of Verbena plant according to this invention originated from crossing a *Verbena hybrida* 'Novaris Rosepink with eye' (♀) (non-patented in the United States and a wild type of Verbena plant *Verbena*

*peruviana* 'VBD' (♂) (non-patented in the United States) native to Brazil.

Initially, 33 seedlings were obtained in the autumn of 1992, from crossing 'Novaris Rosepink with eye' as female parent and a wild type of verbena plant 'VBD' (*Verbena Peruviana f. rosea*) as pollen parent. From this crossing, 8 seedlings were selected in view of their erect growth habit and petal color, propagated by the use of cuttings, and then grown as a trial in flower beds and planters from the spring of 1993 to the autumn of 1994. Finally one plant was selected from these 8 seedlings. The botanical characteristics of the selected one seedling was examined, using the parent varieties 'Novaris Rosepink with eye' and 'VBD' for comparison. As a result, it was concluded that this Verbena is distinguishable from any other variety whose existence is known to us, and is uniform and stable in its characteristics. This new variety of Verbena plant was named 'Sunvivabura'.

In the following description, the color-coding is in accordance with The Horticultural Colour Chart of The Royal Horticultural Society, London, England (R.H.S. Colour Chart). A color chart based on The Japan Color Standard for Horticultural Plant (J.H.S. Color Chart) is also added for reference.

'Novaris Rosepink with eye', used as female parent in the obtaining of this new variety 'Sunvivabura' is commercially available. The main botanical characteristics of Novaris Rosepink with eye, are as follows:

Plant:
*Growth habit.*—Erect.
*Plant width.*—Narrow.
*Plant height.*—Medium.
Stem:
*Diameter.*—Medium.
*Anthocyanin pigmentation.*—Absent.
*Pubescence.*—Present.
*Prickle.*—Absent.
*Branching.*—Medium.
*Subterranean stem.*—Absent.
*Length of internode.*—Medium.
Leaf:
*Phyllotaxis.*—Opposite.
*Shape of blade.*—Hastate.
*Blade of incision.*—Present.
*Depth of blade incision.*—Shallow.
*Shape of leaf margin.*—Crenated.
*Length.*—Medium.
*Width.*—Medium.
*Color.*—Dark yellow green. (R.H.S. Colour Chart No.146A, J.H.S. Color Chart No.3509).
*Pubescence.*—Present.
*Petiole.*—Absent.
Flower:
*Shape of cluster.*—Obconical.
*Spike length.*—Medium.
*Spike diameter.*—Medium.
*Facing direction.*—Upward.
*Outward curvature of petal.*—Slightly curved.
*Diameter.*—Medium.
*Height.*—Long.
*Color of petal.*—Deep pink. (R.H.S. Colour Chart No.52C, J.H.S. Color Chart No.0107).
*Eye color.*—Present.
*Size of eye color.*—Medium.
*Variegation.*—Absent.
*Color presentation.*—Substantially even.
*Overlapping of petals.*—Separate.
*Incision of petal.*—Present.
*Number of petals.*—medium.
*Calyx incision.*—Present.
*Calyx length.*—Medium.
*Anthocyanin pigmentation of calyx limb.*—Present.
*Pistil shape.*—Two lobes.
*Stamen number.*—Medium.
*Anther color.*—Yellowish green.
*Peduncle diameter.*—Thin.
*Peduncle length.*—Medium.
*Number of flowers.*—Many.
*Flower fragrance.*—Absent.
*Flowering time.*—Medium.
*Flowering duration.*—Short.
Physiological and ecological characteristics:
*Tolerance to cold.*—Medium.
*Tolerance to heat.*—Low.
*Resistance to diseases.*—Low.
*Resistance to pests.*—Low.

The pollen parent used in obtaining this new variety 'Sunvivabura' was a wild type of *Verbena peruviana*. The main botanical characteristics of this pollen parent 'VBD' are as follows:

Plant:
*Growth habit.*—Erect.
*Plant width.*—Medium.
*Plant height.*—High. (25–30 cm).
Stem:
*Diameter.*—Medium.
*Anthocyanin pigmentation.*—Present.
*Pubescence.*—Dense.
*Prickle.*—Absent.
*Branching.*—Abundant.
*Subterranean stem.*—Absent.
*Length of internode.*—Medium.
Leaf:
*Phyllotaxis.*—Opposite.
*Shape of blade.*—Hastate.
*Blade incision.*—Present.
*Depth of blade incision.*—Shallow.
*Shape of leaf margin.*—Crenate.
*Length.*—Medium.
*Width.*—Medium.
*Color.*—Dark yellow green (R.H.S. Colour Chart 146A, J.H.S. Color Chart No.3508).
*Pubescence.*—Dense.
*Petiole.*—Absent.
Flower:
*Shape of cluster.*—Turbinate.
*Spike length.*—Medium.
*Spike diameter.*—Medium.
*Facing direction.*—Upward.
*Outward curvature of petal.*—Curved.
*Diameter.*—Medium.
*Height.*—Medium.
*Color of petal.*—Brilliant purple (R.H.S. Colour Chart No.84A, J.H.S. Color Chart No.8305).
*Eye color.*—Present.
*Size of eye color.*—Medium.
*Variegation.*—Absent.
*Color presentation.*—Substantially even.
*Overlapping of petals.*—Separate.
*Incision of petal.*—Present.
*Number of petals.*—medium.
*Calyx incision.*—Present.
*Calyx length.*—Long.
*Anthocyanin pigmentation of calyx limb.*—Present.
*Pistil shape.*—Two lobes.
*Stamen number.*—Medium.
*Anther color.*—Yellowish green.
*Peduncle diameter.*—Thin.
*Peduncle length.*—Short.
*Number of flowers.*—Few.
*Flower fragrance.*—Absent.
*Flowering time.*—Very late.
*Flowering duration.*—Long.
Physiological and ecological characteristics:
*Tolerance to cold.*—High.
*Tolerance to heat.*—High.
*Resistance to diseases.*—High.
*Resistance to pests.*—High.

The new variety of verbena plant 'Sunvivabura' was asexually reproduced by the use of cuttings at the aforementioned Hakushu Nursery Center of SUNTORY Ltd., residing at 29131 Torihara, Hakushu-cho, Kitakoma-gun, Yamanashi-ken, Japan, and the homogeneity and stability thereof were confirmed. The instant plant retains its distinctive characteristics and reproduces true to type in successive generations.

SUMMARY OF THE VARIETY

This new variety of Verbena plant has an erect growth habit with long stems and a good plant height. The plant has many branches and forms flowers abundantly in a spike with a great profusion of blooms. The blooming period is late April to November and the flowering duration is long. The whole plant remains in bloom for a considerable period of time. The flower size is large and the petal color is light purplish pink with further lightening towards the center. The plant is highly tolerant to heat, and has a high resistance to pests and diseases, particularly powdery mildew, and high resistance to rain. Medium resistance to cold is displayed.

The plants described herein were approximately eight months of age and were observed during August while growing in pots. Such plants were being grown at Shimamoto-cho, Oosaka-fu, Japan. Approximately ten weeks are required to produce finished flowering plants following the rooting of cuttings.

DESCRIPTION OF THE VARIETY

The botanical characteristics of the new and distinct variety of Verbena plant, 'Sunvivabura' are as follows:

Plant:
- *Growth habit.*—Erect.
- *Plant extension.*—width — Approximately 30 cm.
- *Plant height.*—High. (25–35 cm).

Stem:
- *Diameter.*—Medium. (2–3 mm).
- *Length.*—Approximately 25 cm.
- *Pubescence.*—Dense.
- *Prickle.*—Absent.
- *Branching.*—Abundant.
- *Subterranean stem.*—Absent.
- *Length of internode.*—Medium. (3–4 cm).

Leaf:
- *Phyllotaxis.*—Opposite.
- *Shape of blade.*—Hastate.
- *Blade incision.*—Pinatilobed.
- *Depth of blade incision.*—Shallow.
- *Shape of leaf margin.*—Dentate to crenate.
- *Length.*—Medium. (3–4 cm).
- *Width.*—Medium. (2–3 cm).
- *Base.*—Wedge-shaped.
- *Apex.*—Acute.
- *Venation pattern.*—Pinnate.
- *Color.*—Moderate olive green. (R.H.S. Colour Chart No.146A, J.H.S. Color Chart No.3508) on the upper surface, and R.H.S. Colour Chart No. 146C on the under surface.
- *Pubescence.*—Moderate in quantity and typical of Verbena.
- *Petiole.*—Present.
- *Petiole diameter.*—Approximately 2 mm.
- *Petiole length.*—Approximately 4 mm.
- *Petiole color.*—R.H.S. Colour Chart No. 144A.

Buds:
- *Shape.*—Club-shaped.
- *Length.*—Approximately 1.1 cm.
- *Diameter.*—Approximately 2 mm.
- *Color.*—R.H.S. Colour Chart No. 144A.

Figure 1:
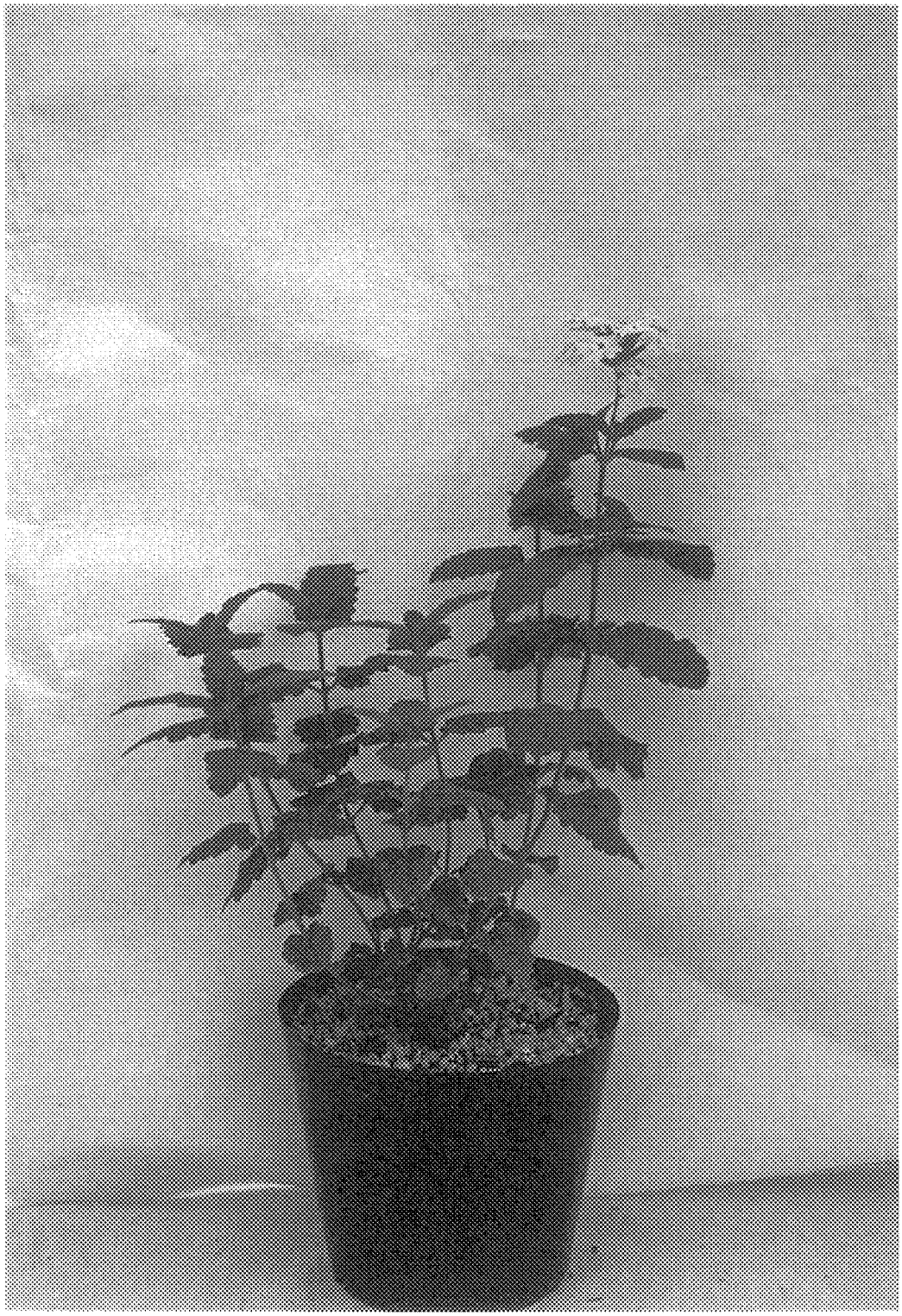
FIG. 1 illustrates a typical plant of the new Verbena variety while growing in a pot.
Figure 2:
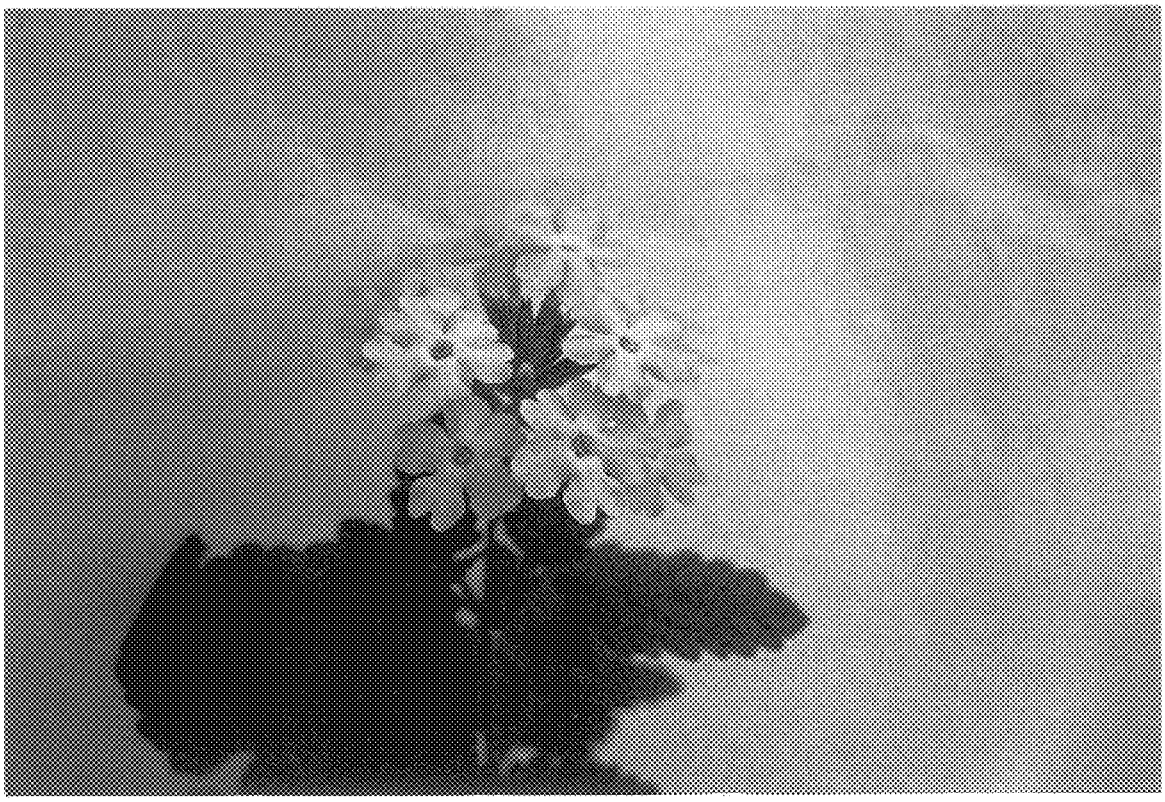
FIG. 2 illustrates a close view of typical foliage and blossoms of the new Verbena variety.

Flower:
- *Shape of cluster.*—Funnel-shaped.
- *Spike length.*—Medium. (5 cm).
- *Spike diameter.*—Medium. (2–3 cm).
- *Facing direction.*—Upward.
- *Outward curvature of petal.*—Slightly curved.
- *Diameter.*—Medium. (20–30 mm).
- *Petal.*—There is one petal having five lobes per flower. Thus the tubular-shaped flower branches into five lobes. The apex of each lobe is emarginated, and the texture of the lobes is matt.
- *Floral tube.*—Approximately 1.8 cm in length.
- *Color of petal.*—Light purplish pink. (R.H.S. Colour Chart No.76A, J.H.S. Color Chart No.8903) on the upper surface, and R.H.S. Colour Chart No. 69C on the under surface.
- *Eye color.*—Absent. However, there is fading of the petal coloration near the point of attachment as illustrated in FIG. 2 to near R.H.S. Colour Chart No. 69C.
- *Variegation.*—Absent.
- *Color presentation.*—Substantially even.
- *Calyx.*—The tubular-shaped calyx divides in five sepals. The sepal apex is acuminate and the sepal margins are smooth. The upper and lower surfaces of the sepals are R.H.S. Colour Chart No. 144A in coloration. The calyx length is approximately 12 mm and the calyx margin is R.H.S. Colour Chart No. 143C in coloration.
- *Pistil number.*—One.
- *Pistil length.*—Approximately 1.5 cm.
- *Stigma.*—Possesses two lobes.
- *Style color.*—R.H.S. Colour Chart No. 144C.
- *Stamen number.*—Commonly four.
- *Anther color.*—Yellowish green.
- *Peduncle diameter.*—Approximately 1.5 mm.
- *Peduncle length.*—Approximately 1.5 cm.
- *Peduncle color.*—R.H.S. Colour Chart No. 144A.
- *Number of flowers.*—Commonly approximately 12 per spike.
- *Flower fragrance.*—Absent.
- *Flowering time.*—Late.
- *Flowering duration.*—Long, with an individual bloom commonly lasting approximately 5 to 8 days.
- *Pollen.*—Formed in a sparse quantity and R.H.S. Colour Chart No. 4B in coloration.
- *Seeds.*—Occasionally formed, generally cylindrical in configuration, approximately 4 mm in length, approximately 1 mm in diameter, and near R.H.S. Colour Chart No. 148A in coloration.

Physiological and ecological characteristics:
- *Tolerance to cold.*—High with the plant having withstood a temperature of −5° C.
- *Tolerance to heat.*—High.
- *Resistance to diseases.*—High particularly with respect to powdery mildew.
- *Resistance to pests.*—High particularly with respect to aphids.

This new variety of Verbena plant is most suitable for flower bedding and potting, particularly in planters, and is further excellent for use as a ground cover.

What is claimed is:

1. A new and distinct variety of Verbena plant, substantially as herein illustrated and described, characterized particularly as to novelty by (A) an erect growth habit, (B) a plentiful amount of flowers in a spike with a great profusion of blooms, (C) a long flowering duration, (D) a large flower size and light purplish pink petal color with further lightening towards the center, and (E) having high resistance to rain, heat, cold, drought, diseases and pests.

* * * * *